(12) United States Patent
Lui et al.

(10) Patent No.: US 8,344,151 B2
(45) Date of Patent: Jan. 1, 2013

(54) PROCESS FOR THE PREPARATION OF 4-AMINOBUT-2-ENOLIDES STARTING FROM 4-ALKOXYFURAN-2(5H)-ONE OR 4-ARYLALKOXYFURAN-2(5H)-ONE

(75) Inventors: Norbert Lui, Odenthal (DE); Jens-Dietmer Heinrich, Burscheid (DE)

(73) Assignee: Bayer Cropscience AG, Monheim (DE)

( * ) Notice: Subject to any disclaimer, the term of this patent is extended or adjusted under 35 U.S.C. 154(b) by 123 days.

(21) Appl. No.: 12/974,988

(22) Filed: Dec. 21, 2010

(65) Prior Publication Data

US 2011/0152534 A1 Jun. 23, 2011

Related U.S. Application Data

(60) Provisional application No. 61/290,385, filed on Dec. 28, 2009.

(30) Foreign Application Priority Data

Dec. 23, 2009 (EP) ..................... 09180603

(51) Int. Cl.
*C07D 405/00* (2006.01)
*C07D 307/02* (2006.01)
(52) U.S. Cl. ..................... 546/284.4; 549/295
(58) Field of Classification Search ............... 546/284.4; 549/295
See application file for complete search history.

(56) References Cited

U.S. PATENT DOCUMENTS

| RE28,242 E | 11/1974 | Boosen |
| 2009/0253749 A1 | 10/2009 | Jeschke et al. |
| 2010/0190990 A1 | 7/2010 | Lui et al. |

FOREIGN PATENT DOCUMENTS

| CA | 1 225 094 | 8/1987 |
| CH | 503 722 | 2/1971 |
| EP | 0 153 615 | 9/1985 |
| EP | 0 539 588 | 5/1993 |
| EP | 0 042 496 | 4/2009 |
| GB | 1 256 847 | 12/1971 |
| WO | 2007/115644 | 10/2007 |

OTHER PUBLICATIONS

Dorwald F. A. (Side Reactions in Organic Synthesis, 2005, Wiley: VCH, Weinheim p. IX of Preface p. 1-15).*
European Search Report Based on Application EP 09 18 0603 Dated Apr. 23, 2010.
International Search Report Based on Application No. PCT/EP2010/070202 Dated May 2, 2011.
Momose et al.; "An efficient Synthesis and the Eschenmoser-Mannich Reaction of N-Substituted 4-Amino-2(5H)-Furanones"; Heterocycles; 1988; vol. 27; No. 8; pp. 1907-1923.
Kemmler et al.; "Inter- and Intramolecular [2+2]-Photocycloaddition of Tetronates—Stereoselectivity, Mechanism, Scope and Synthetic Applications"; Eur. J. Org. Chem.; 2004; vol. 22; pp. 4582-4595; Wiley VCH Verlag GmbH & Co. KGaA, Weinheim.
Shandala et al.; "Reaction of Methyl Tetronate with some Amines, Synthesis of Substituted 4-Aminobut-2-enolides"; J. Heterocyclic Chem.; Nov.-Dec. 1984; vol. 21; No. 6; pp. 1753-1754.
Greenhill et al.; "A New and Easier Route to Tetronic Acid"; Tetrahedron Letters No. 31; 1974; pp. 2683-2684; Pergamon Press; Great Britain.
Schmidt et al.; A Convenient Synthesis of 2,4(3H,5H)-Furandione (Beta-Tetronic Acid)1a; Synthetic Communications; 1981; vol. 11; No. 5; pp. 385-390; Marcel Dekker, Inc.
Marrian et al.; "The Structure of Anhydrotetronic Acid"; J. Chem. Soc.; 1947; pp. 1365-1369.
Mulholland et al.; "A Synthesis of Tetronic Acid [Furan-2(3H),4(5H)-dione} and Three Analogues"; 1972; vol. 9/10; pp. 1225-1231.

* cited by examiner

*Primary Examiner* — Nizal Chandrakumar
(74) *Attorney, Agent, or Firm* — Baker Donelson Bearman Caldwell & Berkowitz, PC

(57) ABSTRACT

Process for the preparation of 4-aminobut-2-enolide compounds of the formula (I):

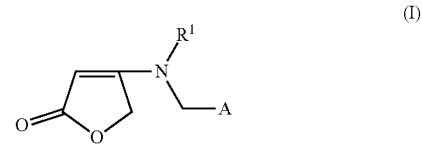

comprising
reaction of a 4-alkoxyfuran-2(5H)-one compound or 4-arylalkoxyfuran-2(5H)-one compound of the formula (II)

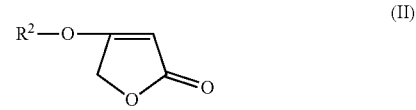

with an amine of the formula (III)

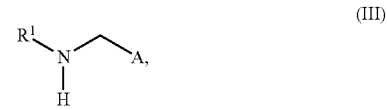

in which $R^1$, $R^2$ and A have the definitions given in the description, in the presence of a Brønstedt acid.

12 Claims, No Drawings

PROCESS FOR THE PREPARATION OF 4-AMINOBUT-2-ENOLIDES STARTING FROM 4-ALKOXYFURAN-2(5H)-ONE OR 4-ARYLALKOXYFURAN-2(5H)-ONE

CROSS REFERENCE TO RELATED APPLICATIONS

This application claims priority from EP 09180603.4 filed Dec. 23, 2009 and U.S. Ser. No. 61/290,385 filed Dec. 28, 2009, the contents of which are incorporated herein by reference in their entireties.

BACKGROUND OF THE INVENTION

1. Field of the Invention

The present invention relates to a process for the preparation of 4-aminobut-2-enolides starting from 4-alkoxyfuran-2(5H)-one or 4-arylalkoxyfuran-2(5H)-one.

2. Description of Related Art

Certain substituted 4-aminobut-2-enolide compounds are known as insecticidally effective compounds from EP-A-0 539 588 and WO 2007/115644. They can be synthesized by various methods.

Thus, for example, Heterocycles Vol. 27, No. 8, pages 1907 to 1923 (1988) and EP-A-0 539 588 describe that enaminocarbonyl compounds (3) can be prepared from anhydrous tetronic acid (1) and an amine (2), as shown in Scheme 1. However, this process is not very suitable for the large-scale industrial production of enaminocarbonyl compounds since the anhydrous tetronic acid (1) cannot be produced in a cost-effective manner.

Scheme 1:

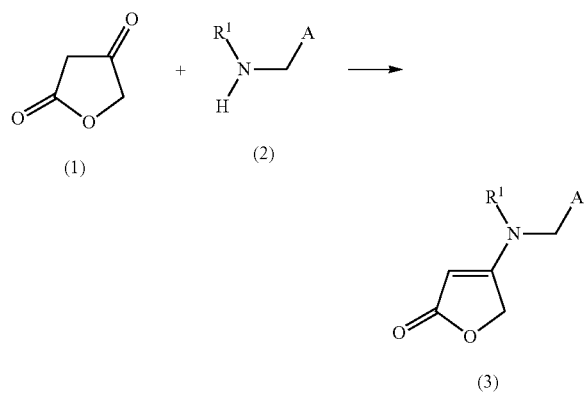

To date, tetronic acid has not been commercially available in relatively large amounts, meaning that it has to be prepared starting from acetoacetic ester via bromination and subsequent hydrogenation (cf. Synthetic Communication, 11(5), pages 385 to 390 (1981)) for use in the process described above. The relatively low yield of tetronic acid (usually less than 40%) and the condition that tetronic acid must be anhydrous gives rise to high costs.

A further process for the preparation of tetronic acid is described in Swiss Patent Specification 503 722. 4-Chloroacetoacetic ester is reacted with an aromatic amine to give 3-arylaminocrotono-lactone, the tetronic acid being liberated following subsequent treatment with mineral acid. The tetronic acid can be isolated only by distillation under a high vacuum, which is disadvantageous for the large-scale industrial use of this process.

EP-A-0 153 615 likewise describes a multi-stage process for the preparation of tetronic acid which starts from 2,4-dichloroacetoacetic esters and which is not very suitable for large-scale industrial production. This process requires many complex stages and produces the desired tetronic acid in a comparatively moderate yield of 65%.

A further process for the preparation of tetronic acid starting from malonic esters and chloroacetyl chloride is known from J. Chem. Soc. Perkin Trans. 1 (1972), 9/10, pages 1225-1231. This process produces the desired target compound, but with a yield of only 43%.

Tetrahedron Letters, No. 31, pages 2683 and 2684 (1974) describes inter alia the preparation of tetronic acid, which is shown in Scheme 2. The starting material used here is dimethyl acetylenedicarboxylate.

Scheme 2:

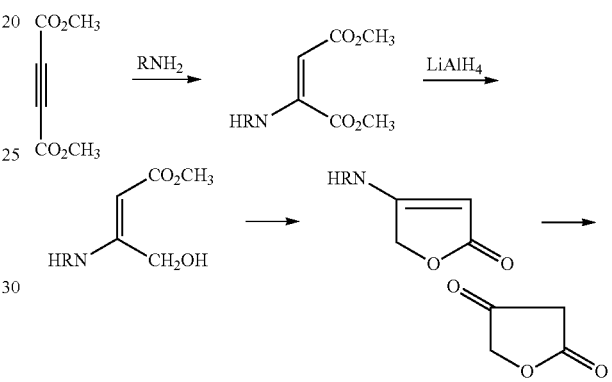

A disadvantage of this process is the low overall yield of only 30%, and the use of expensive starting materials, such as, for example, lithium aluminium hydride (LiAlH$_4$).

WO 2007/115644 describes the preparation of specific 4-aminobut-2-enolides. For example of 4-[[(6-chloropyridin-3-yl)methyl](3,3-dichloroprop-2-en-l-yl)amino]furan-2(5H)-one by reacting 4-[[(6-chloropyridin-3-yl)methyl]amino] furan-2 (5 H)-one with 3-bromo -1,1-dichloroprop -1-ene or by reacting 4-[[2-fluoroethyl)amino]furan-2(5H)-one with 2-chloro-5-chloromethylpyridine. The reactions are preferably carried out with hydrides of lithium or sodium. Here too, these substrates are expensive and can only be handled with difficulty for safety reasons.

A further process for the preparation of substituted 4-aminobut-2-enolides is described by Mowafak. et al. in J. Heterocyclic Chem., 21, pages 1753-1754 (1984). This process starts from methyl tetronate, the desired compounds being prepared as a result of reaction with amines. However, this described exchange of the methoxy group described therein via a "Michael Addition" can only be carried out with electron-rich cyclic or primary amines, which is demonstrated by the example in the experimental section of this patent application.

SUMMARY OF THE INVENTION

Starting from this, it is therefore the object to provide a process for the preparation of 4-aminobut-2-enolide compounds of the formula (I) which produces the 4-aminobut-2-enolide compounds with a high yield and sufficiently high purity and which can be carried out easily and cost-effectively. Additionally, a tetronic acid derivative which can be manufactured cost-efficiently and which is easy to work with should be employed in said process.

We have now found a process for the preparation of 4-aminobut-2-enolide compounds which avoids the aforementioned disadvantages and which can be carried out simply and cost-effectively, in particular because the 4-aminobut-2-enolide compounds according to the invention are obtained with good yields and in high purity, meaning that complex work-up and/or purification of the direct reaction product is usually not required.

The invention therefore provides the process described below for the preparation of 4-aminobut-2-enolide compounds of the formula (I):

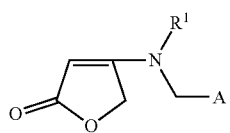
(I)

in which $R^1$ and A are the chemical groups defined below.

The process according to the invention for the preparation of 4-aminobut- 2-enolide compounds of the formula (I) involves the reaction of a 4-alkoxyfuran-2(5H)-one compound 4-arylalkoxyfuran-2(5H)-one of the formula (II)

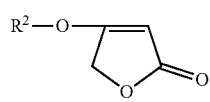
(II)

with an amine of the formula (III)

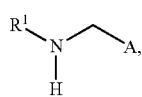
(III)

in which $R^1$ is hydrogen, $C_{1-12}$-alkyl, $C_{1-12}$-haloalkyl, $C_{2-12}$-alkenyl, $C_{2-12}$-haloalkenyl, $C_{2-6}$-alkynyl, $C_{3-8}$-cycloalkyl, $C_{3-8}$-cycloalkyl-$C_{1-6}$-alkyl, $C_{3-8}$-halocycloalkyl, $C_{1-12}$alkoxy, $C_{1-6}$-alkyloxy-$C_{1-6}$-alkyl, $C_{3-8}$-halocycloalkyl-$C_{1-6}$-alkyl or aryl-$C_{1-6}$-alkyl, $R^1$ is preferably $C_{1-6}$-alkyl, $C_{1-6}$-haloalkyl, $C_{2-6}$-alkenyl, $C_{2-6}$-haloalkenyl, $C_{2-6}$-alkynyl, $C_{3-8}$-cycloalkyl, $C_{3-8}$-cycloalkyl-$C_{1-6}$-alkyl, $C_{3-8}$-halocycloalkyl, $C_{3-8}$-halocycloalkyl-$C_{1-6}$-alkyl or $C_{1-6}$-alkyloxy-$C_{1-6}$-alkyl, particularly preferably methyl, ethyl, propyl, propylene, propylene, vinyl, allyl, propargyl, cyclopropyl, $C_{1-6}$-alkyloxy-$C_{1-6}$-alkyl, 2-fluoroethyl, 2,2-difluoroethyl or 2-fluorocyclopropyl, very particularly preferably methyl, ethyl, n-propyl, n-prop-2-enyl, n-prop-2-ynyl, cyclopropyl, methoxyethyl, 2-fluoroethyl or 2,2-difluoroethyl;

$R^2$ is $C_{1-12}$-alkyl, aryl-$C_{1-6}$-alkyl, $R^2$ is preferably $C_1$-$C_6$-alkyl, aryl-$C_{1-6}$-alkyl, particularly preferably benzyl, methyl or ethyl; and A is pyrid-2-yl, pyrid-4-yl or pyrid-3-yl, which are optionally substituted in the 6-position by F, Cl, Br, $CH_3$, $CF_3$, or $OCF_3$, is pyridazin-3-yl, which is optionally substituted in the 6-position by Cl or $CH_3$, is pyrazin-3-yl, 2-chloropyrazin-5-yl or is 1,3-thiazol-5-yl optionally substituted in the 2-position by Cl or $CH_3$, is pyrimidinyl, pyrazolyl, thiophenyl, oxazolyl, isoxazolyl, 1,2,4-oxadiazolyl, isothiazolyl, 1,2,4-triazolyl or 1,2,5-thiadiazolyl, which is optionally substituted by F, Cl, Br, CN, $NO_2$, $C_{1-4}$-alkyl, $C_{1-3}$-alkylthio $C_{1-3}$-alkylsulphonyl, where each of the radicals $C_{1-4}$-alkyl, $C_{1-3}$-alkylthio and $C_{1-3}$-alkylsulphonyl is substituted by F and/or chlorine, or is a substituted heterocyclyl of the following formula

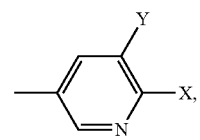

in which

X is halogen, $C_{1-12}$-alkyl or $C_{1-12}$-haloalkyl, and

Y is halogen, $C_{1-12}$-alkyl, $C_{1-12}$-haloalkyl, $C_{1-12}$-haloalkoxy, azido or CN;

A is preferably a substituted heterocyclyl selected from 6-fluoropyrid-3-yl, 6-chloropyrid-3-yl, 6-bromopyrid-3-yl, 6-methylpyrid-3-yl, 6-trifluoromethylpyrid-3-yl, 6-trifluoromethoxypyrid-3-yl, 6-chloro-1,4-pyridazin-3-yl, 6-methyl-1,4-pyridazin-3-yl, 2-chloro-1,3-thiazol-5-yl or 2-methyl-1,3-thiazol-5-yl, 2-chloropyrimidin-5-yl, 2-trifluoromethylpyrimidin-5-yl, 5,6-difluoropyrid-3-yl, 5-chloro-6-fluoropyrid-3-yl, 5-bromo-6-fluoropyrid-3-yl, 5-iodo-6-fluoropyrid-3-yl, 5-fluoro-6-chloropyrid-3-yl, 5,6-dichloropyrid-3-yl, 5-bromo-6-chloropyrid-3-yl, 5-iodo-6-chloropyrid-3-yl, 5-fluoro-6-bromopyrid-3-yl, 5-chloro-6-bromopyrid-3-yl, 5,6-dibromopyrid-3-yl, 5-fluoro-6-iodopyrid-3-yl, 5-chloro-6-iodopyrid-3-yl, 5-bromo-6-iodopyrid-3-yl, 5-methyl-6-fluoropyrid-3-yl, 5-methyl-6-chloropyrid-3-yl, 5-methyl-6-bromopyrid-3-yl, 5-methyl-6-iodopyrid-3-yl, 5-difluoromethyl-6-fluoropyrid-3-yl, 5-difluoromethyl-6-chloropyrid-3-yl, 5-difluoromethyl-6-bromopyrid-3-yl or 5-difluoromethyl-6-iodopyrid-3-yl, A is particularly preferably a substituted heterocyclyl selected from 6-fluoropyrid-3-yl, 6-chloropyrid-3-yl, 6-bromopyrid-3-yl, 6-chloro-1,4-pyridazin-3-yl, 2-chloro-1,3-thiazol-5-yl, 2-chloropyrimidin-5-yl, 5-fluoro -6-chloropyrid-3-yl , 5,6-dichloropyrid-3-yl, 5-bromo -6-chloropyrid-3-yl, 5-fluoro-6-bromopyrid-3-yl, 5-chloro-6-bromopyrid-3-yl, 5,6-dibromopyrid-3-yl, 5-methyl-6-chloropyrid-3-yl, 5-chloro-6-iodopyrid-3-yl or 5-difluoromethyl-6-chloropyrid-3-yl, A is very particularly preferably a substituted heterocyclyl selected from 6-chloropyrid-3-yl, 6-bromopyrid-3-yl, 6-chloro-1,4-pyridazin-3-yl, 2-chloro -1,3-thiazol-5-yl, 5-fluoro -6-chloropyrid-3-yl and 5-fluoro -6-bromopyrid-3-yl, in the presence of a Brønstedt acid.

DETAILED DESCRIPTION OF A PREFERRED EMBODIMENT

Surprisingly, it has been found that, in the reaction or conversion according to the invention, the exchange of the alkoxy radical in the compound of the formula (II) for the amine of the formula (III) takes place in very good yields. In absence of a Brønstedt acid, no conversion takes place, as demonstrated in the comparative example. Furthermore, it is surprising that the tetronic acid does not dimerize under the reaction conditions, although such a dimerization was to be expected according to J. Chem. Soc. (1947) page 1365.

The conversion according to the invention can be carried out in the presence of solvents (diluents). The solvent is preferably used in an amount such that the reaction mixture remains readily stirrable during the entire process. Solvents suitable for carrying out the process or conversion according to the invention are all organic solvents inert under the reaction conditions. According to the invention, solvents are also understood as meaning mixtures of pure solvents.

Solvents suitable according to the invention are in particular halohydrocarbons, such as chloro-hydrocarbons (e.g. tetrachloroethylene, tetrachloroethane, dichloropropane, methylene chloride, dichlorobutane, chloroform, tetrachloromethane, trichloroethane, trichloroethylene, pentachloro-ethane, difluorobenzene, 1,2-dichloroethane, chlorobenzene, bromobenzene, dichlorobenzene, chlorotoluene, trichlorobenzene), ethers (e.g. ethyl propyl ether, methyl tert-butyl ether, n-butyl ether, anisole, phenetole, cyclohexyl methyl ether, dimethyl ether, diethyl ether, dimethyl glycol diphenyl ether, dipropyl ether, diisopropyl ether, di-n-butyl ether, diisobutyl ether, diisoamyl ether, ethylene glycol dimethyl ether, isopropyl ethyl ether, methyl tert-butyl ether, tetrahydrofuran, methyltetrahydrofuran, dioxane, dichlorodiethyl ether, and polyethers of ethylene oxide and/or propylene oxide, nitrohydrocarbons (e.g. nitromethane, nitroethane, nitropropane, nitrobenzene, chloronitrobenzene, o-nitrotoluene), nitriles (e.g. acetonitrile, methylnitrile, propionitrile, butyronitrile, isobutyronitrile, benzonitrile, m-chlorobenzonitrile) and also tetrahydrothiophene dioxide and dimethyl sulphoxide, tetramethylene sulphoxide, dipropyl sulphoxide, benzyl methyl sulphoxide, diisobutyl sulphoxide, dibutyl sulphoxide, diisoamyl sulphoxide; sulphones, such as dimethyl, diethyl, dipropyl, dibutyl, diphenyl, dihexyl, methyl ethyl, ethyl propyl, ethyl isobutyl and tetramethylene sulphone, aliphatic, cycloaliphatic or aromatic hydrocarbons (e.g. pentane, n-hexane, n-heptane, n-octane, nonane so-called "white spirits" with components having boiling points in the range for example from 40° C. to 250° C., cymene, benzine fractions within a boiling interval from 70° C. to 190° C., cyclohexane, methylcyclohexane, petroleum ether, naphtha, octane, benzene, toluene, xylene; esters, such as methyl, ethyl, butyl and isobutyl acetate, and dimethyl, dibutyl and ethylene carbonate), amides (e.g. hexamethylenephosphorotriamide, formamide, N,N-dimethylacetamide, N-methylformamide, N,N-dimethylformamide, N,N-dipropylformamide, N,N-dibutylformamide, N-methylpyrrolidine, N-methylcaprolactam, 1,3-dimethyl-3,4,5,6-tetrahydro-2(1H)-pyrimidine, octylpyrrolidone, octylcaprolactam, 1,3-dimethyl-2-imidazolinedione, N-formylpiperidine, N,N'-1,4-diformylpiperazine), and aliphatic alcohols (e.g. methanol, ethanol, n-propanol and isopropanol and n-butanol) or mixtures thereof.

For the process according to the invention or the conversion, the solvents used are preferably dioxane, butyronitrile, propionitrile, acetonitrile, butyl acetate, DME, toluene, methyl-THF, dichlorobenzene, chlorobenzene, n-heptane, isobutanol, n-butanol, ethanol, methyl tert-butyl ether, isopropyl ethyl ether and mixtures thereof.

Depending on the starting compounds used, the process according to the invention or the conversion can be carried out without a diluent, i.e. without the addition of solvents.

Brønstedt acids suitable according to the invention are in principle all organic and inorganic acids. Brønstedt acids preferred according to the invention are phosphoric acid ($H_3PO_4$), sulphuric acid ($H_2SO_4$), hydrochloric acid (HCl), hydrobromic acid (HBr), hydrofluoric acid (HF), potassium hydrogensulphate ($KHSO_4$), trifluoroacetic acid, acetic acid, methanesulphonic acid and p-toluene-sulphonic acid.

According to the invention, particular preference is given to phosphoric acid, sulphuric acid, potassium hydrogensulphate and trifluoroacetic acid.

The Brønstedt acid may be present either in anhydrous form or else in water-containing form, for example as 85% strength phosphoric acid or 37% strength hydrochloric acid. For economic reasons, it is preferred to use the commercially available acid concentration.

The molar ratio of the Brønstedt acid used to the amine of the formula (III) can vary. Preferably, the molar ratio of Brønstedt acid to the amine of the formula (III) is in the range from about 10:0.6 to about 1:1.5, in particular from about 5:0.9 to 1:1.2, specifically from about 2:1 to about 1:1.1.

The process according to the invention can generally be carried out in vacuo, at atmospheric pressure or under superatmospheric pressure.

The temperatures used can vary depending on the starting materials used. The conversion according to the invention or the process can be carried out at temperatures in the range from about 20° to about 200° C., preferably at temperatures in the range from about 20° C. to about 150° C.

The stoichiometry of the compounds of the formula (II) and (III) used can vary within wide ranges. The molar ratio of the compound of the formula (II) to the amine of the formula (III) used can be about 1:0.5 to about 1:10, in particular about 1:1 to about 1:6, specifically about 1:1.05 to about 1:2. The use of relatively large amounts of compound of the formula (III) is possible in principle, but is disadvantageous for economic reasons.

If the conversion is carried out in a solvent, the solvent can be removed after the end of the reaction by distillation. This can take place under atmospheric pressure or reduced pressure at room temperature or elevated temperatures.

After the end of the reaction, the Brønstedt acid can be removed by extraction with water. The isolation of the desired compounds of the formula (I) can take place by customary methods.

4-Methoxyfuran-2(5H)-one derivatives of the formula (II) are known in some cases and/or can be prepared by customary methods.

The preparation of compound of the formula (II) in which $R^2$ is methyl is described, for example, in J. Heterocyclic Chem. 21, 1753 (1984). Further preparations of compounds of the formula (II) are described, for example, in European Journal of Organic Chemistry (2004), (22), page 4582-4595.

If not defined otherwise herein, and within the context of the present invention, the term "alkyl", either alone or in combination with further terms, such as, for example, haloalkyl, alkoxyalkyl, cycloalkylalkyl, halocycloalkylalkyl and arylalkyl, is understood as meaning a radical of a saturated, aliphatic hydrocarbon group having 1 to 12 carbon atoms, which may be branched or unbranched. Examples of $C_{1-12}$-alkyl radicals are methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1-ethylpropyl, 1,2-dimethylpropyl, hexyl n-heptyl, n-octyl, n-nonyl, n-decyl, n-undecyl and n-dodecyl. Of these alkyl radicals, $C_{1-6}$-alkyl radicals are particularly preferred. Particular preference is given to $C_{1-4}$-alkyl radicals, specifically methyl and ethyl.

If not defined otherwise herein, and within the context of the present invention, the term "alkenyl" is understood as meaning a linear or branched $C_{2-12}$-alkenyl radical which has at least one double bond, for example vinyl, allyl, 1-propenyl, isopropenyl, 1-butenyl, 2-butenyl, 3-butenyl, 1,3-butanedienyl, 1-pentenyl, 2-pentenyl, 3-pentenyl, 4-pentenyl, 1,3-pentanedienyl, 1-hexenyl, 2-hexenyl, 3-hexenyl, 4-hexenyl, 5-hexenyl and 1,4-hexanedienyl. Of these, preference is given to $C_{2-6}$-alkenyl radicals and particular preference is given to $C_{2-4}$-alkenyl radicals.

If not defined otherwise herein, and within the context of the present invention, the term "alkynyl" is understood as meaning a linear or branched $C_{2-12}$-alkynyl radical which has at least one triple bond, for example ethynyl, 1-propynyl and propargyl. Of these, preference is given to $C_{2-6}$-alkynyl radicals and particular preference is given to $C_{3-4}$-alkynyl radicals. The alkynyl radical may here also have at least one double bond.

If not defined otherwise herein, and within the context of the present invention, the term "cycloalkyl" is understood as meaning a $C_{3-8}$-cycloalkyl radical, for example cyclopropyl, cyclobutyl, cyclopentyl, cyclohexyl, cycloheptyl and cyclooctyl. Of these, preference is given to $C_{3-6}$-cycloalkyl radicals.

If not defined otherwise herein, and within the context of the present invention, the term "aryl" is understood as meaning an aromatic radical having 6 to 14 carbon atoms, preferably phenyl.

If not defined otherwise herein, and within the context of the present invention, the term "arylalkyl" is understood as meaning a combination of "aryl" and "alkyl" radicals defined according to the invention, the radical generally being bonded via the alkyl group. Examples thereof are benzyl, phenylethyl or a-methylbenzyl, with benzyl being particularly preferred.

If not defined otherwise herein, and within the context of the present invention, "radicals substituted by halogen", for example haloalkyl, are understood as meaning radicals mono- or polyhalogenated up to the maximum possible number of substituents. In the case of polyhalogenation, the halogen atoms may be identical or different. Here, halogen is fluorine, chlorine, bromine or iodine, in particular fluorine, chlorine or bromine.

If not defined otherwise herein, and within the context of the present invention, the term "alkoxy", either alone or in combination with further terms, such as, for example, haloalkoxy, is understood in the present case as meaning an O-alkyl radical, the term "alkyl" having the aforementioned meaning.

Optionally substituted radicals may be mono- or polysubstituted, where, in the case of a poly-substitution, the substituents may be identical or different.

The present invention is illustrated by reference to the examples below, without limiting the invention to these.

PREPARATION EXAMPLES

Comparative Example

Analogous to that Described in J. Heterocyclic Chem., 21, pages 1753-1754 (1984)

0.3 g (2.6 mmol) of 4-methoxyfuran-2(5H)-one and 0.54 g (2.6 mmol) 5 g of N-[(6-chloropyridin-3-yl(methyl)-2,2-difluoroethylamine are initially introduced in 3 ml of dioxane and heated under reflux for 15 h. No reaction takes place.

Example According to the Invention 0.3 g (2.6 mmol) of 4-methoxyfuran-2(5H)-one and 0.54 g (2.6 mmol) of N-[(6-chloropyridin-3-yl)methyl)-2,2-difluoroethylamine are initially introduced in 3 ml of dioxane, and 1 ml of 32% strength hydrochloric acid is added. The mixture is then heated under reflux for 8 h. The reaction mixture is poured onto water and extracted twice with methylene chloride. The methylene chloride phase is dried over sodium sulphate and then the solvent is removed in vacuo. This gives 0.6 g of 4-[ [ (6-chloropyridin-3-yl)methyl] (2,2-difluoro ethyl)amino] furan-2 (5 H)-one (79% yield).

$^1$H-NMR (CDCl$_3$, 298K) δ:3.53 (td, 2H), 4.52 (s, 2H), 4.82 (s, 2H), 4.83 (s, 1H), 5.96 (tt, 1H), 7.37 (d, 1H), 7.55 (dd, 1H), 8.27 (d, 1H)

The invention claimed is:
1. A process for the preparation of a 4-aminobut-2-enolide compound of formula (I)

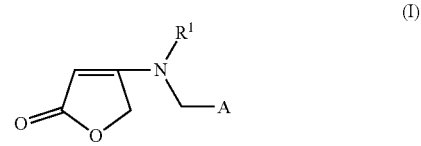

comprising reacting a 4-alkoxyfuran-2(5H)-one compound or 4-arylalkoxyfuran-2(5H)-one compound of formula (II)

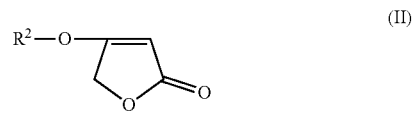

with an amine of formula (III)

in which
$R^1$ is hydrogen, $C_{1-12}$-alkyl, $C_{2-12}$-alkenyl, $C_{2-6}$-alkynyl, $C_{3-8}$-cycloalkyl, $C_{3-8}$-cycloalkyl-$C_{1-6}$-alkyl, $C_{1-12}$-alkoxy, $C_{1-6}$-alkyloxy-$C_{1-6}$-alkyl, aryl-$C_{1-6}$-alkyl, 2-fluoroethyl, 2,2-difluoroethyl, or 2-fluorocyclopropyl;
$R^2$ is $C_{1-12}$-alkyl, or aryl-$C_{1-6}$-alkyl; and
A is pyrid-2-yl, pyrid-4-yl or pyrid-3-yl, which are optionally substituted in the 6-position by F, Cl, Br, CH$_3$, CF$_3$, or OCF$_3$, or is a substituted heterocyclyl of the following formula

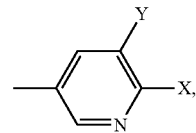

in which
X is halogen or $C_{1-12}$-alkyl, and
Y is halogen or $C_{1-12}$-alkyl;
in the presence of a Brønstedt acid.
2. The process according to claim 1, wherein, in formula (III),
$R^1$ is $C_{1-6}$-alkyl, $C_{2-6}$-alkenyl, $C_{2-6}$-alkynyl $C_{3-8}$-cycloalkyl, $C_{3-8}$-cycloalkyl-$C_{1-6}$-alkyl, or $C_{1-6}$-alkyloxy-$C_{1-6}$-alkyl; and
A is selected from 6-fluoropyrid-3-yl, 6-chloropyrid-3-yl, 6-bromopyrid-3-yl, 6-methylpyrid-3-yl, 6-trifluoromethylpyrid-3-yl, 6-trifluoromethoxypyrid-3-yl, 6-chloro-1,4-pyridazin-3-yl, 6-methyl-1,4-pyridazin-3-yl, 2-chloro-1,3-thiazol-5-yl or 2-methyl-1,3-thiazol-5-yl, 2-chloropyrimidin-5-yl, 2-trifluoromethylpyrimidin-5-yl, 5,6-difluoropyrid-3-yl, 5-chloro-6-fluoropyrid-3-yl, 5-bromo-6-fluoropyrid-3-yl, 5-iodo-6-fluoropyrid-3-yl, 5-fluoro-6-chloropyrid-3-yl, 5,6-dichloropyrid-3-yl, 5-bromo-6-chloropyrid-3-yl, 5-iodo-6-chloropyrid-3-yl, 5-fluoro-6-bromopyrid-3-yl, 5-chloro-6-bromopyrid-3-yl, 5,6-dibromopyrid-3-yl, 5-fluoro-6-iodopyrid-3-yl, 5-chloro-6-iodopyrid-3-yl, 5-bromo-6-iodopyrid-3-yl, 5-methyl-6-fluoropyrid-3-yl, 5-methyl-6-chloropyrid-3-yl, 5-methyl-6-bromopyrid-3-yl, 5-methyl-6-iodopyrid-3-yl, 5-difluoromethyl-6-fluoropyrid-3-yl, 5-difluoromethyl-6-chloropyrid-3-yl, 5-difluoromethyl-6-bromopyrid-3-yl or 5-difluoromethyl-6-iodopyrid-3-yl.

3. The process according to claim 1, wherein the Brønstedt acid is selected from the group consisting of phosphoric acid, sulphuric acid, hydrochloric acid, hydrobromic acid, hydrofluoric acid, potassium hydrogensulphate, trifluoroacetic acid, acetic acid, methanesulphonic acid and p-toluenesulphonic acid.

4. The process according to claim 1, wherein the molar ratio of the compound of the formula (H) to the amine of the formula (III) used is 1:0.5 to 1:10.

5. The process according to claim 1, wherein the molar ratio of the Brønstedt acid used to the amine of the formula (III) is in the range from about 5:0.8 to about 1:1.5.

6. The process according to claim 2, wherein the Brønstedt acid is selected from the group consisting of phosphoric acid, sulphuric acid, hydrochloric acid, hydrobromic acid, hydrofluoric acid, potassium hydrogensulphate, trifluoroacetic acid, acetic acid, methanesulphonic acid and p-toluenesulphonic acid.

7. The process according to claim 2, wherein the molar ratio of the compound of the formula (H) to the amine of the formula (III) used is 1:0.5 to 1:10.

8. The process according to claim 3, wherein the molar ratio of the compound of the formula (H) to the amine of the formula (III) used is 1:0.5 to 1:10.

9. The process according to claim 2, wherein the molar ratio of the Brønstedt acid used to the amine of the formula (III) is in the range from about 5:0.8 to about 1:1.5.

10. The process according to claim 3, wherein the molar ratio of the Brønstedt acid used to the amine of the formula (III) is in the range from about 5:0.8 to about 1:1.5.

11. The process according to claim 4, wherein the molar ratio of the Brønstedt acid used to the amine of the formula (III) is in the range from about 5:0.8 to about 1:1.5.

12. The process of claim 1, wherein formula (III) is N-[(6-chloropyridin-3-yl)methyl]-2,2-difluoroethylamine.

* * * * *